(12) United States Patent
Ren

(10) Patent No.: US 12,409,126 B2
(45) Date of Patent: Sep. 9, 2025

(54) GINSENOSIDE-CONTAINING COMPOSITION, DAILY-USE CHEMICAL AND USE THEREOF

(71) Applicants: InCipirit Tech (Guangzhou) Co., Ltd., Guangdong (CN); cBioMey (Guangzhou) Technology Co., Ltd., Guangdong (CN)

(72) Inventor: Shaohua Ren, Guangdong (CN)

(73) Assignees: InCipirit Tech (Guangzhou) Co., Ltd., Guangzhou (CN); cBioMey (Guangzhou) Technology Co., Ltd., Guangzhou (CN)

( * ) Notice: Subject to any disclaimer, the term of this patent is extended or adjusted under 35 U.S.C. 154(b) by 0 days.

(21) Appl. No.: 18/434,921

(22) Filed: Feb. 7, 2024

(65) Prior Publication Data
US 2024/0285499 A1    Aug. 29, 2024

(30) Foreign Application Priority Data
Feb. 23, 2023   (CN) .......................... 202310168658.2

(51) Int. Cl.
| | | |
|---|---|---|
| *A61K 8/63* | (2006.01) | |
| *A61K 8/49* | (2006.01) | |
| *A61K 8/64* | (2006.01) | |
| *A61Q 7/00* | (2006.01) | |

(52) U.S. Cl.
CPC .............. *A61K 8/63* (2013.01); *A61K 8/4953* (2013.01); *A61K 8/64* (2013.01); *A61Q 7/00* (2013.01); *A61K 2800/782* (2013.01)

(58) Field of Classification Search
CPC .......... A61K 8/63; A61K 8/4953; A61K 8/64; A61K 2800/782; A61K 2800/5922; A61Q 7/00; A61Q 5/02; A61Q 5/12; A61P 17/14
See application file for complete search history.

(56) References Cited

FOREIGN PATENT DOCUMENTS

| | | | |
|---|---|---|---|
| CN | 111249163 A | 6/2020 | |
| CN | 113197911 A | 8/2021 | |
| CN | 114025770 A | 2/2022 | |
| KR | 102021463 B1 * | 9/2019 | ........... A61K 31/704 |

OTHER PUBLICATIONS

Machine translation of KR-102021463-B1, 31 pages. (Year: 2019).*
1st Office Action of counterpart Chinese Patent Application No. 202310168658.2 issued on Dec. 7, 2023.
Notice of Allowance of counterpart Chinese Patent Application No. 202310168658.2 issued on Jan. 7, 2024.

* cited by examiner

*Primary Examiner* — Aaron J Kosar

(57) ABSTRACT

The present invention belongs to the technical field of daily-use chemicals, and discloses a ginsenoside-containing composition, which includes the following components in parts by weight: 0.001-0.05 parts of palmitoyl tetrapeptide-7, 0.001-0.05 parts of blue copper peptide, 0.1-5 parts of ectoin, and 0.05-5 parts of a ginsenoside composition. According to the present invention, excellent fast acting and consistently-increased hair growth, hair loss prevention and hair development effects are achieved through preferred compounding of the ginsenoside composition and multiple polypeptides, etc. Meanwhile, the present invention further provides use of the composition and a daily-use chemical using the composition.

8 Claims, 12 Drawing Sheets

GINSENOSIDE-CONTAINING COMPOSITION, DAILY-USE CHEMICAL AND USE THEREOF

CROSS REFERENCE TO RELATED APPLICATIONS

The present application claims the benefit of Chinese Patent Application No. 202310168658.2 filed on Feb. 23, 2023, the contents of which are incorporated herein by reference in their entirety.

TECHNICAL FIELD

The present invention belongs to the technical field of daily-use chemicals, and particularly relates to a ginsenoside-containing composition, a daily-use chemical and use thereof.

BACKGROUND

Radix et Rhizoma Ginseng extracts have been widely known as effective ingredients for hair loss prevention and hair growth, as follows:

CN115154387A relates to a preparation method of a hair essence, in particular to a hair essence for promoting hair growth and a preparation method thereof; the hair essence is mild in compatibility and comprehensive in efficacy, and reserves effective ingredients and biological activities of plant extracts and various proteins to the maximum degree, with formulation ideas of enhancing hair quality and nutrition of hair follicles, improving differentiation of hair follicle skin, highlighting the hair care and hair loss prevention efficacy and overcoming the shortcomings of the prior art; the hair essence includes the following raw material components: glycosylglycerol, dihydroquercetin glucoside, methyl propanediol, hydrolyzed soy protein, hydrolyzed wheat protein, panthenol, tocopheryl acetate, adenosine, Radix et Rhizoma Ginseng extracts, peony root extracts, larch extracts, sodium hyaluronate and deionized water; and various raw material components in mass percentages are 6-8.5% of glycosylglycerol, 4-9.5% of dihydroquercetin glucoside, 4-8% of methyl propanediol, 0.5-3% of hydrolyzed soy protein, 0.5-3% of hydrolyzed wheat protein, 0.2-1% of panthenol, 0.2-1% of tocopheryl acetate, 0.2-1% of adenosine, 0.3-1% of Radix et Rhizoma Ginseng extracts, 0.3-1% of peony root extracts, respectively.

CN113577003A relates to a three-in-one hair growth and hair care shampoo, which includes a core component and also includes auxiliary components, and the core component contains Semen sesami nigrum, NotoRadix et Rhizoma Ginseng Radix et Rhizoma, Rosae Rugosae Flos, fructus cnidii, Foeniculi Fructus, cherry, Astragali Radix, Jasminum sambac, rhizoma zingiberis recens, Polygoni multiflori radix, Radix et Rhizoma Ginseng, Radix Angelicae Sinensis, Spina Gleditsiae, black rice, herba leonuri, Polyporus umbellatus (Pers.), Ligusticum chuanxiong Hort. A preparation method of the three-in-one hair growth and hair care shampoo is also disclosed. The present invention achieves the beneficial effects that hair follicles can be activated, nutrients necessary for hair growth are provided, hair drying, yellowing and bifurcating are improved, dandruff and grease can be effectively cleaned, multiple functions are achieved at the same time without inhibiting each other, and consistent and consistent use can be realized.

CN113197911A provides use of a ginsenoside composition in preparing a medicament for preventing and curing hair loss by acting on hair follicle tissues. The ginsenoside composition consists of ginsenoside Rg1, ginsenoside Re and ginsenoside CK, wherein the ginsenoside Rg1 and the ginsenoside Re are main active ingredients, and the ginsenoside CK is an auxiliary ingredient. Secondly, the present invention also provides use of the aforementioned ginsenoside composition in preparing a medicament for increasing activity of hair follicle tissues, wherein the medicament is directly applied or sprayed onto the scalp to promote hair follicles in a telogen stage to enter a regeneration period and promote hair growth. Thirdly, the present invention also provides use of the aforementioned ginsenoside composition in preparing a medicament for increasing activity of hair follicle tissues cultured in vitro, wherein the preparation of the ginsenoside composition into a tissue culture solution to act on the hair follicle tissues cultured in vitro can increase the activity of the cultured hair follicle tissues and significantly increase the survival rate of transplanted hair follicles.

CN112546056A discloses a composition for treating chemotherapy-induced peripheral neuropathies and application thereof, and belongs to the field of medicine. The present invention provides a composition for treating chemotherapy-induced peripheral neuropathies, including ginsenoside Rg1 and fucoidin. The composition of the present invention can significantly inhibit the expression of pro-inflammatory factors such as TNF-α, IL-1β and IL-6, thereby producing an anti-inflammatory pro-restorative effect on peripheral nerves and enhancing resistance; and in addition, the composition of the present invention can also significantly improve microcirculation disorders, upregulate SR-A expression, and in turn enhance the phagocytosis and clearance ability of HMGB1 by macrophages, inhibit TF overexpression, alleviate microcirculation disorders and neuropathic pains induced by chemotherapy drugs in a multi-target multi-mechanism mode, and fundamentally inhibit CIPN development, thereby achieving safe and effective therapeutic objectives, and providing a new therapeutic strategy for clinic.

The applicant has found, upon investigation, that: combinations of different ginsenosides (including but not limited to Radix et Rhizoma Ginseng native glucoside, diol-type ginsenoside, triol-type ginsenoside, diol-type Radix et Rhizoma Ginseng secondary glycoside, triol-type ginsenoside) have different effects on epidermal keratinocytes and dermal papilla cell proliferative effects, 5α-reductase activity and alkaline phosphatase activity, which means that different combinations have different effects on the aspects of cytotoxicity, hair loss prevention, hair growth and hair development.

Meanwhile, the following reference documents also suggest use of other related ingredients of the present invention in different fields, as follows:

CN115282094A discloses a composition for hair growth and a preparation method and application thereof, and belongs to the technical field of medicinal cosmetics. According to the composition, aiming at different targets of hair loss, active matters with different hair loss mechanisms are rationally matched and prepared into compositions, synergistic interaction is realized, and the triple efficacy of hair loss prevention and hair growth, hair fixation as well as hair blackening are combined;

it was recorded in the specification that: the biopolysaccharide is β-glucan; the hair growth peptides include one or more of oligopeptide-54, octapeptide-2, decapeptide-18, myristoyl pentapeptide-17, myristoyl pentapeptide-16, myristoyl pentapeptide-7, myristoyl pentapeptide-4, myristyl hexapeptide-16, myristoyl tetrapeptide-12, palmitoyl hexapeptide-25 and tripeptide-2; the hair fixation peptides include one or more of biotin tripeptide-1, acetyl tetrapeptide-3, palmitoyl tripeptide-1 and decapeptide-10; and the hair blackening peptides include one or more of copper peptide, acetyl hexapeptide-1 and palmitoyl tetrapeptide-10;

CN112218612A discloses a composition and method for modifying hair. The method includes: coating hair fibers with a composition including ethylene carbonate and a diol selected from at least one of propylene glycol, 1,3-propanediol, dipropylene glycol, tripropylene glycol, and a mixture thereof; and contacting the coated hair with a heating appliance at a temperature of at least 150° C. for a sufficient time to modify the hair fibers;

it is recorded in the specification that the peptides or commercial mixtures containing the same are for example, selected from but not limited to the group consisting of peptides for cosmetics, such as palmitoyl tetrapeptide-7, and palmitoyl oligopeptide;

CN115670953A discloses a hair growth essence and a preparation method thereof, wherein the hair growth essence includes the following components in weight percentages: 89.24% of water, 7% of PEG-400, 1% of dextran, 0.5% of citrulline, 1% of MSM, 0.01% of biotin tripeptide-1, 0.35% of blue copper peptide, 0.5% of panthenol, 0.1% of zinc gluconate, 0.15% of phenoxyethanol, and 0.15% of chlorphenesin. The present invention further relates to a preparation method of the aforementioned hair growth essence. The components involved in the present invention are safe, free of toxic and side effects and scientific in compatibility, contain PEG-400, citrulline, biotin tripeptide-1, blue copper peptide, zinc gluconate and the like effective ingredients, and can effectively strengthen hair roots, regulate metabolism and promote new hair growth; meanwhile, the major component PEG-400 has a dispersive effect; and the blue copper peptide has the effects of improving the skin regeneration capacity, promoting skin absorption, achieving deep skin waking, etc.

CN114712259A discloses a hair loss prevention and hair fixation composition, a preparation method thereof and an application product. The hair loss prevention and hair fixation composition of the present invention adopts a preliposome concentrate to conduct liposomal encapsulation on niacinamide, creatine, tripeptide-1 copper, magnolol and honokiol to form loaded liposomes, a hair-loss-preventing fermentation filtrate is compounded to be applied into hair-loss-preventing products, blood circulation in scalp can be promoted, the composition is rapidly absorbed into deep hair follicles, and the hair loss prevention and itch prevention effects of the active matters are fully exerted. The hair loss prevention and hair fixation product containing the present composition can be used for repairing microecological balance of scalp skin and effectively reducing production of scalp scale; and the viability of hair follicles is maintained, the growth period of hair shafts is prolonged, hair loss is reduced, hair follicle cells entering the dormant period grow again, the number of hair follicles in the growth period is increased, and the advantage of continuously improving hair loss is achieved.

The tripeptide-1 copper described above is the blue copper peptide.

CN115363987A discloses a scalp care formula containing collagen and ectoin, and belongs to the technical field of daily-use chemical products. The scalp care formula of the present invention is made from the following raw materials in parts by weight: 1-2 parts of recombinant type III humanized collagen, 1-10 parts of ectoin, 5.62-78 parts of an adjuvant, and 10-92.38 parts of water. In the scalp care formula of the present invention, the recombinant type III humanized collagen has a very strong anti-inflammatory repair effect, can supplement the scalp with collagen, eliminates scalp inflammation, and repairs scalp damage; and after being compounded with ectoin, the ectoin can promote collagen absorption. The scalp care formula of the present invention is simple in ingredients and has low irritation to the scalp.

It can be seen that palmitoyl tetrapeptide-7, ectoin and blue copper peptide do not act directly on hair, but are used for promoting scalp nutrition so as to achieve the purpose of improving hair loss, hair growth, hair development and the like aspects.

The technical problem solved by the present invention is: how to achieve the best effects of hair loss prevention, hair growth and hair development, especially a fast-acting effect of improving the effects continuously with respect to the preferred realization of multiple polypeptides and mixing of the best combinations of ginsenoside extracts.

SUMMARY OF THE INVENTION

In view of the shortcomings of the prior art, an objective of the present invention is to provide a ginsenoside-containing composition, which achieves excellent fast acting and continuously-increased hair growth, hair loss prevention and hair development effects through preferred ginsenoside compositions, compounding of multiple polypeptides, etc.

Meanwhile, the present invention further provides use of the composition and a daily-use chemical using the composition.

To achieve the objective of the present invention, the present invention adopts the following technical solution: a ginsenoside-containing composition, including the following components in parts by weight:
    0.001-0.05 parts of palmitoyl tetrapeptide-7,
    0.001-0.05 parts of blue copper peptide,
    0.1-5 parts of ectoin, and
    0.05-5 parts of a ginsenoside composition;
    the ginsenoside composition is any one of one or more groups of ginsenoside compositions in N1, N2, N4, N5, N6;
    the N1 includes the following components:
    12-28 wt % of ginsenoside Rg1,
    10-16 wt % of ginsenoside Re,
    12-28 wt % of ginsenoside Rb1,
    13-22 wt % of ginsenoside Rc,
    13-22 wt % of ginsenoside Rb2, and
    7-13 wt % of ginsenoside Rd;
    the N2 includes the following components:
    30-50 wt % of ginsenoside Rg1, and
    48-72 wt % of ginsenoside Re;
    the N4 includes the following components:
    8-16 wt % of 20(S)-ginsenoside Rg2,
    7-15 wt % of 20(R)-ginsenoside Rg2,
    17-25 wt % of 20(S)-ginsenoside Rh1,
    16-23 wt % of 20(R)-ginsenoside Rh1,
    5-12 wt % of ginsenoside Rk3, and
    16-26 wt % of ginsenoside Rh4;
    the N5 includes the following components:
    20-40 wt % of ginsenoside Rk3, and
    60-80 wt % of ginsenoside Rh4;
    the N6 includes the following components:
    16-21 wt % of 20(S)-ginsenoside Rg3,
    32-50 wt % of 20(R)-ginsenoside Rg3,
    4-8 wt % of ginsenoside Rk1, 8-15 wt % of ginsenoside Rg5,
3-7 wt % of 20(S)-ginsenoside Rh2,
11-19 wt % of 20(R)-ginsenoside Rh2,
0.1-1 wt % of ginsenoside Rk2, and
0.5-1.5 wt % of ginsenoside Rh3;
and a sum of all components in N1, N2, N4, N5, N6 is 100%.

In the aforementioned ginsenoside-containing composition, the N1 includes the following components:
18-22 wt % of ginsenoside Rg1,
12-15 wt % of ginsenoside Re,
18-22 wt % of ginsenoside Rb1,
15-19 wt % of ginsenoside Rc,
16-20 wt % of ginsenoside Rb2, and
9-11 wt % of ginsenoside Rd;
the N2 includes the following components:
35-45 wt % of ginsenoside Rg1, and
55-65 wt % of ginsenoside Re;
the N4 includes the following components:
10-13 wt % of 20(S)-ginsenoside Rg2,
8-13 wt % of 20(R)-ginsenoside Rg2,
18-23 wt % of 20(S)-ginsenoside Rh1,
17-21 wt % of 20(R)-ginsenoside Rh1,
6-10 wt % of ginsenoside Rk3, and
18-22 wt % of ginsenoside Rh4;
the N5 includes the following components:
25-35 wt % of ginsenoside Rk3, and
65-75 wt % of ginsenoside Rh4;
the N6 includes the following components:
18-20 wt % of 20(S)-ginsenoside Rg3,
37-43 wt % of 20(R)-ginsenoside Rg3,
5-7 wt % of ginsenoside Rk1,
9-13 wt % of ginsenoside Rg5,
4-6 wt % of 20(S)-ginsenoside Rh2,
13-17 wt % of 20(R)-ginsenoside Rh2,
0.2-0.8 wt % of ginsenoside Rk2, and
0.7-1.2 wt % of ginsenoside Rh3;
and a sum of all components in N1, N2, N4, N5, N6 is 100%.

In the aforementioned ginsenoside-containing composition, the ginsenoside compositions contain at least one of N1, N2, N4 and at least one of N4, N5, N6.

In the aforementioned ginsenoside-containing composition, the composition includes the following components in parts by weight:
0.01-0.03 parts of palmitoyl tetrapeptide-7,
0.01-0.03 parts of blue copper peptide,
0.5-2 parts of ectoin, and
0.05-1 parts of a ginsenoside composition.

In the aforementioned ginsenoside-containing composition, the composition includes the following components in parts by weight:
0.02 parts of palmitoyl tetrapeptide-7,
0.02 parts of blue copper peptide,
1 part of ectoin, and
0.25 parts of a ginsenoside composition.

Meanwhile, the present invention further discloses a daily-use chemical acting on hair, including any one of the aforementioned compositions; and the composition accounts for 0.01-50 wt % of the total weight of the daily-use chemical.

In the aforementioned daily-use chemical acting on hair, the composition accounts for 0.01-20 wt % of the total weight of the daily-use chemical, and preferably, the composition accounts for 0.1-10 wt % of the total weight of the daily-use chemical.

In the aforementioned daily-use chemical acting on hair, the daily-use chemical is shampoo, a hair conditioner, lyophilized powder, an essence, shampoo spray, hair cream, hair lotion.

Finally, the present invention further discloses use of the composition according to any one described above in the daily-use chemical as a hair loss prevention active ingredient and use in the daily-use chemical as a hair growth and hair development active ingredient.

Compared with the prior art, the present invention has the following beneficial effects:
the present invention achieves highly efficient, fast and sustained multi-target comprehensive hair loss prevention and hair development effects and conducts all-around scalp health care at the same time by preferred ginsenoside compositions and compounding of multiple polypeptides; and moisture is locked to the inside, and the barrier is consolidated to the outside. Meanwhile, soothing and calming are realized, scalp discomforts are relieved, a healthy and young scalp environment is created for tough and beautiful hair.

In particular, the preferred ginsenoside compositions of the present invention have a hair loss prevention and hair development action mechanism of activating and inhibiting: promoting VEGF (vascular endothelial growth factor) expression, promoting dermal papilla cell proliferation, activating alkaline phosphatase expression, activating glucocorticoid receptor GR, effectively inhibiting 5α-reductase, inhibiting DKK-1 expression and restoring Wnt pathways; and compared with minoxidil, the ginsenoside compositions have superior effects in the aspects of restoring the Wnt pathways and activating the glucocorticoid receptor GR;

The aforementioned functions of the preferred ginsenoside compositions of the present invention synergize with palmitoyl tetrapeptide-7, blue copper peptide and ectoin, and excellent fast-acting and continuously-increased hair loss prevention, hair growth and hair development effects are finally achieved.

The ginsenoside compositions of the present invention are the best ingredients obtained after repeated screening. In particular, by conducting experiments on various different combinations on epidermal keratinocyte and dermal papilla cell proliferation effects, 5α-reductase activity and alkaline phosphatase activity, we have found that:
the cytotoxicity of the ginsenoside composition N5, the ginsenoside composition N6 and the ginsenoside composition N7 is higher than that of other Radix et Rhizoma Ginseng extracts.

The ginsenoside composition N4 has the effect of promoting the epidermal keratinocyte proliferation effect, and it is also found to have the effect of promoting the epidermal keratinocyte proliferation effect when a dermal papilla cell and epidermal keratinocyte double-layer culture system is used for testing.

The ginsenoside composition N1, the ginsenoside composition N2 and the ginsenoside composition N4 have the effect of inhibiting 5α-reductase activity.

The ginsenoside composition N4, the ginsenoside composition N5 and the ginsenoside composition N6 have a promoting effect on the activity of alkaline phosphatase of cultured dermal papilla cells.

It means that: the ginsenoside composition N1, the ginsenoside composition N2 and the ginsenoside composition N4 are effective for preventing male hair loss, while the ginsenoside composition N4, the ginsenoside composition N5 and the ginsenoside composition N6 have a hair development effect.

Overall speaking, we believe that the ginsenoside composition N4 performs the best among most of the tests, and is most suitable for addition to the daily-use chemical as the best choice for hair loss prevention and hair growth.

Through parallel clinical tests, the formula of compounding N4 with palmitoyl tetrapeptide-7, blue copper peptide and ectoin can achieve the hair loss prevention and hair growth effects more quickly within 28 days under the same additive dose compared to the N4, and the 84-day continuously-increased effect of the former is significantly better than that of the latter. Therefore, among the optimal daily-use chemicals, the N4 is recommended for compounding with palmitoyl tetrapeptide-7, blue copper peptide and ectoin.

BRIEF DESCRIPTION OF DRAWINGS

FIG. 14 is a photomicrograph of the scalp of parts of subjects in a second part of human tests;
and
FIG. 15 is a photograph4 of hair of parts of subjects in the second part of human tests.

DETAILED DESCRIPTION

Figure 1:
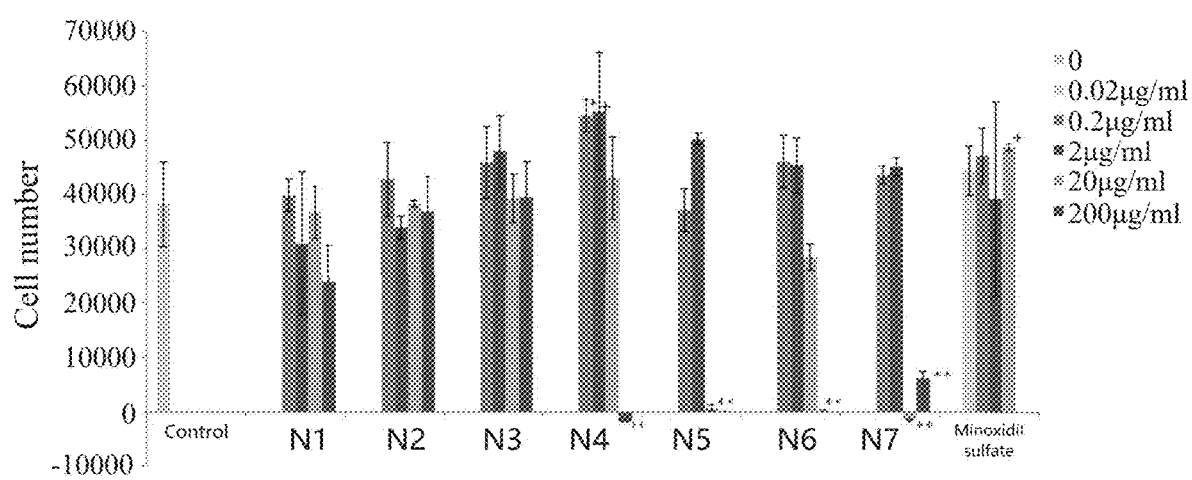
FIG. 1 is a graph showing the effects of ginsenoside compositions on the epidermal keratinocyte proliferation effect;
mean value+standard deviation n=3; + represents p<0.1; * represents p<0.05; ** represents p<0.01 vs Control; the same as follows.

The technical solutions of the present invention are further illustrated below by specific embodiments. It should be understood by those skilled in the art that the embodiments are merely to aid in understanding the present invention and should not be construed as particularly limiting the present invention.

If no specific experimental steps or conditions is indicated in the examples, it shall be carried out according to the operations or conditions of the conventional experimental steps described in the literature in the art. All of the used agents or instruments which are not specified with the manufacturer are conventional commercially-available reagents products.

In order to better illustrate the advantages of the present invention, the present invention is divided into two parts to express the advantages of the solution of the present invention;

the first part is to investigate the trend of change in performance of different types of ginsenoside compositions to determine the optimal ginsenoside composition;

and the second part is that various groups of ginsenoside compositions are compounded with palmitoyl tetrapeptide-7, blue copper peptide and ectoin to investigate the compounding synergy between the ginsenoside compositions and palmitoyl tetrapeptide-7, blue copper peptide and ectoin.

Part I Study of Ginsenoside Compositions

Example 1 disclosed is a ginsenoside composition including components as shown in Table 1 below:

TABLE 1

| Ginsenoside formula table (in wt %) | | | | | |
|---|---|---|---|---|---|
| | N1 | N1-2 | N1-3 | N1-4 | N1-5 |
| Ginsenoside Rg1 | 20 | 17 | 24 | 18 | 22 |
| Ginsenoside Re | 14 | 15 | 10 | 15 | 12 |
| Ginsenoside Rb1 | 20 | 17 | 25 | 22 | 22 |
| Ginsenoside Rc | 18 | 21 | 13 | 15 | 15 |
| Ginsenoside Rb2 | 18 | 17 | 20 | 20 | 20 |
| Ginsenoside Rd | 10 | 13 | 8 | 10 | 9 |
| Total | 100 | 100 | 100 | 100 | 100 |

Example 2

Disclosed is a ginsenoside composition including components as shown in Table 2 below:

TABLE 2

| Ginsenoside formula table (in wt %) | | | | | |
|---|---|---|---|---|---|
| | N2 | N2-2 | N2-3 | N2-4 | N2-5 |
| Ginsenoside Rg1 | 40 | 30 | 50 | 35 | 45 |
| Ginsenoside Re | 60 | 70 | 50 | 65 | 55 |
| Total | 100 | 100 | 100 | 100 | 100 |

Example 3

Disclosed is a ginsenoside composition (N3), including the following ingredients:
30 wt % of ginsenoside Rb1,
26 wt % of ginsenoside Rc,
27 wt % of ginsenoside Rb2, and
17 wt % of ginsenoside Rd.

Example 4

Disclosed is a ginsenoside composition, including ingredients as shown in Table 3 below:

TABLE 3

| Ginsenoside formula table (in wt %) | | | | | | |
|---|---|---|---|---|---|---|
| | N4 | N4-1 | N4-2 | N4-3 | N4-4 | N4-5 |
| 20(S)-ginsenoside Rh1 | 22 | 23 | 19 | 25 | 23 | 21 |
| 20(S)-ginsenoside Rg2 | 14 | 15 | 10 | 16 | 13 | 13 |
| 20(R)-ginsenoside Rg2 | 11 | 15 | 15 | 9 | 13 | 13 |
| 20(R)-ginsenoside Rh1 | 21 | 22 | 23 | 19 | 19 | 21 |
| Ginsenoside Rk3 | 10 | 9 | 7 | 12 | 10 | 10 |
| Ginsenoside Rh4 | 22 | 16 | 26 | 19 | 22 | 22 |
| Total | 100 | 100 | 100 | 100 | 100 | 100 |

Example 5

Disclosed is a ginsenoside composition, including ingredients as shown in Table 4 below:

TABLE 4

| Ginsenoside formula table (in wt %) | | | | | |
|---|---|---|---|---|---|
| | N5 | N5-2 | N5-3 | N5-4 | N5-5 |
| Ginsenoside Rk3 | 29 | 20 | 40 | 25 | 35 |
| Ginsenoside Rh4 | 71 | 80 | 60 | 75 | 65 |
| Total | 100 | 100 | 100 | 100 | 100 |

Example 6

Disclosed is a ginsenoside composition, including ingredients as shown in Table 5 below:

TABLE 5

| Ginsenoside formula table (in wt %) | | | | | |
|---|---|---|---|---|---|
| | N6 | N6-2 | N6-3 | N6-4 | N6-5 |
| 20(S)-ginsenoside Rg3 | 19 | 16 | 21 | 18 | 20 |
| 20(R)-ginsenoside Rg3 | 40.4 | 45.5 | 42.5 | 41.5 | 41 |
| Ginsenoside Rk1 | 7 | 4 | 8 | 5 | 7 |
| Ginsenoside Rg5 | 11 | 13 | 9 | 13 | 11 |
| 20(S)-ginsenoside Rh2 | 5 | 3 | 7 | 4 | 6.5 |
| 20(R)-ginsenoside Rh2 | 16 | 17 | 11 | 17 | 13 |
| Ginsenoside Rk2 | 0.6 | 0.1 | 1 | 0.5 | 0.5 |
| Ginsenoside Rh3 | 1 | 1.4 | 0.5 | 1 | 1 |
| Total | 100 | 100 | 100 | 100 | 100 |

Example 7

Disclosed is a ginsenoside composition, including the following ingredients:
13 wt % of ginsenoside Rk1,
23 wt % of 20(S)-ginsenoside Rh2,
13 wt % of 20(R)-ginsenoside Rh2,
20 wt % of ginsenoside Rk2, and
31 wt % of ginsenoside Rh3.

Preparation Method of Examples 1-7 precisely weighing various components, and performing blending.

Performance Test

Ginsenoside compositions N1, N2, N3, N4, N5, N6, N7 were dissolved with dimethyl sulfoxide (DMSO), and samples at concentrations of 20 mg/ml, 2 mg/ml, 0.2 mg/ml, 0.02 mg/ml were prepared respectively;

in addition, minoxidil sulfate (Sigma-Aldrich) was dissolved with DMSO to prepare solutions at concentrations of 2 mg/ml, 0.2 mg/ml, 0.02 mg/ml, 0.002 mg/ml respectively as positive controls.

Meanwhile, finasteride (Sigma-Aldrich) was also prepared with DMSO into a solution at a concentration of 1.5 µg/ml (4 µM);

1. Effect of Radix Et Rhizoma Ginseng Extracts on Epidermal Keratinocyte and Dermal Papilla Cell Proliferation Effects A human epidermal keratinocyte solution at a concentration of 200,000 cells/ml was inoculated into a 96-well cell culture plate (n=3) at an amount of 100 µl/well for culture for one day. 1 µl/well of Radix et Rhizoma Ginseng extracts 1-7, a positive control (minoxidil sulfate) and a blank control (DMSO) were then added respectively, and then continued culture was performed for 3 days. Afterwards, 10 µl/well of Cell Counting Kit-8 (Dojindo Laboratories) was added for continued culture for another 2 hours, and cell counting was performed with a microplate reader (450 nm, Mix0).

The effect of ginsenoside compositions on the epidermal keratinocyte proliferation effect could refer to FIG. 1;

In FIG. 1, ginsenoside composition N4 significantly increased the cell number at concentrations of 0.2 µg/ml, 2 µg/ml (p values were P<0.05, P<0.1, respectively).

Its effect was stronger than that of the positive control Minoxidil sulfate (0.02 µg/ml, 0.2 µg/ml, 2 µg/ml, 20 µg/ml). Meanwhile, the ginsenoside compositions N4, N5, N6, N7 at a concentration of 200 µg/ml resulted in significant reduction in cell number. The Ginsenoside composition N1 at a concentration of 200 µg/ml also resulted in reduction in cell number;

A human dermal papilla cell solution at a concentration of 100,000 cells/cell was inoculated into a 96-well cell culture plate (n=3) at an amount of 100 µl/well for culture for one day. Proliferation and counting of dermal papilla cells were also performed. The samples to be tested had a concentration ranged from 0.2 µg/ml to 200 µg/ml, and minoxidil sulfate had a concentration ranged from 0.02 µg/ml to 20 g/ml.

Figure 2:
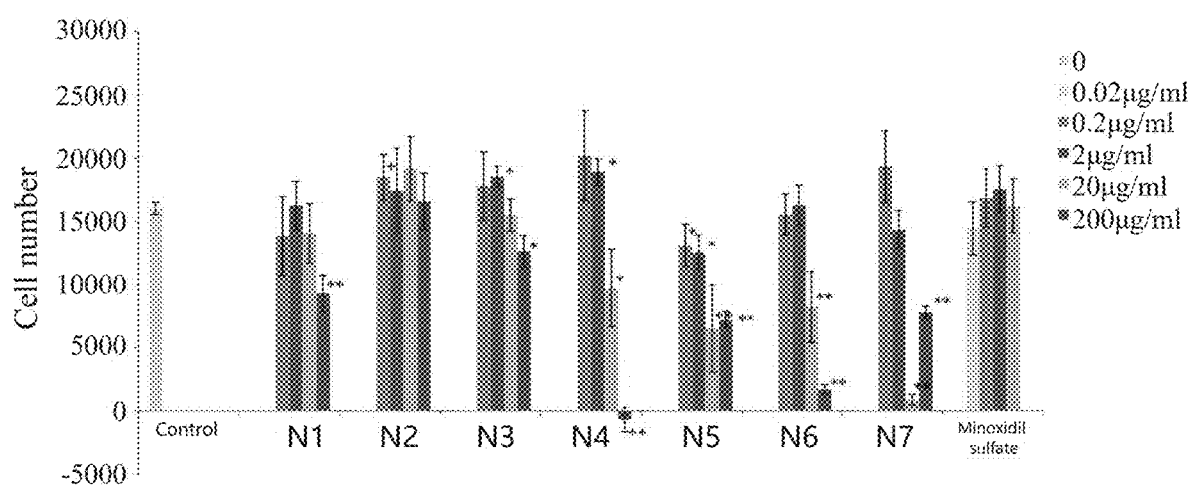
FIG. 2 is a graph showing the effects of ginsenoside compositions on the dermal papilla cell proliferation effect.

Referring to FIG. 2, FIG. 2 showed the effects of ginsenoside compositions on the dermal papilla cell proliferation effect;

the ginsenoside composition N4 at a concentration of 2 µg/ml had an effect of increasing the cell number (P<0.05).

Its effect was stronger than that of the positive control Minoxidil sulfate (0.02 µg/ml, 0.2 µg/ml, 2 µg/ml, 20 µg/ml). The ginsenoside composition N3 at a concentration of 2

µg/ml also had an effect of increasing the cell number (P<0.05). The ginsenoside composition N2 at a concentration of 0.2 µg/ml was observed to have a tendency to increase the cell number (P<0.1). The ginsenoside compositions N4 and N6 at a concentration of 200 µg/ml resulted in a significant reduction in cell number. The ginsenoside compositions N1, 3, 5, 7 at 200 µg/ml also resulted in reduction in cell number.

According to the method, water-soluble tetrazolium salts of a highly-sensitive water-soluble yellow formazan product were reduced under the action of intracellular dehydrogenases, and the absorbance of the resulting water-soluble yellow formazan product was determined at 450 nm to calculate the viable cell number. The cell number and the amount of formazan had a linear relationship.

2. Effect of Radix Et Rhizoma Ginseng Extracts on Epidermal Keratinocyte Proliferation in a Dermal Papilla Cell and Epidermal Keratinocyte Double-Layer Culture System 500 µl of human epidermal keratinocytes (30,000 cells/ml) were added to each well of MULTIWELL 24well, followed by the addition of 1.0 µm of cell culture inserts for culture for 1 day. 300 µl of dermal papilla cells (20,000 cells/ml) had been added in the 1.0 µm of cell culture inserts. each 1 µl/well of the Radix et Rhizoma Ginseng extracts 1-7, the positive control (minoxidil sulfate) and the blank control (DMSO) was then added for continued culture for 3 days. After removal of the 1.0 µm of cell culture inserts, 50 µl/well of Cell Counting Kit-8 (Dojindo Laboratories) was added for continued culture for 2 hours, and the cell number was determined using a microplate reader (450 nm, Mix0).

Figure 3:
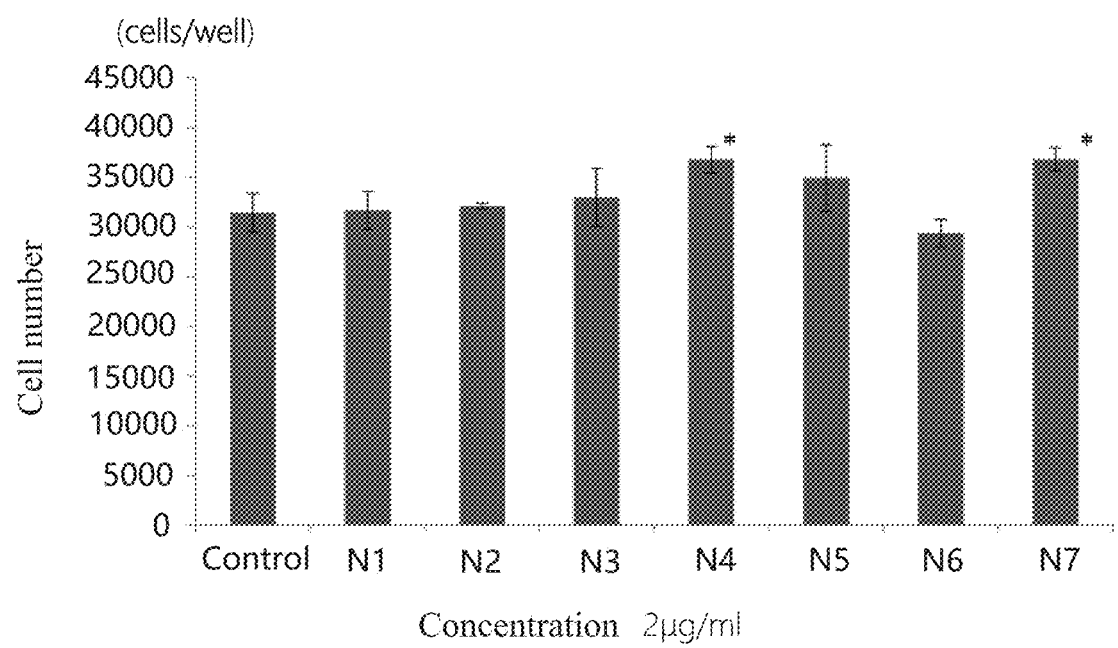
FIG. 3 is a graph showing the effects of Radix et Rhizoma Ginseng extracts on epidermal keratinocyte proliferation in a dermal papilla cell and keratinocyte double-layer culture system under the condition that the ginsenoside composition is at a concentration of 2 μg/ml.
Figure 4:
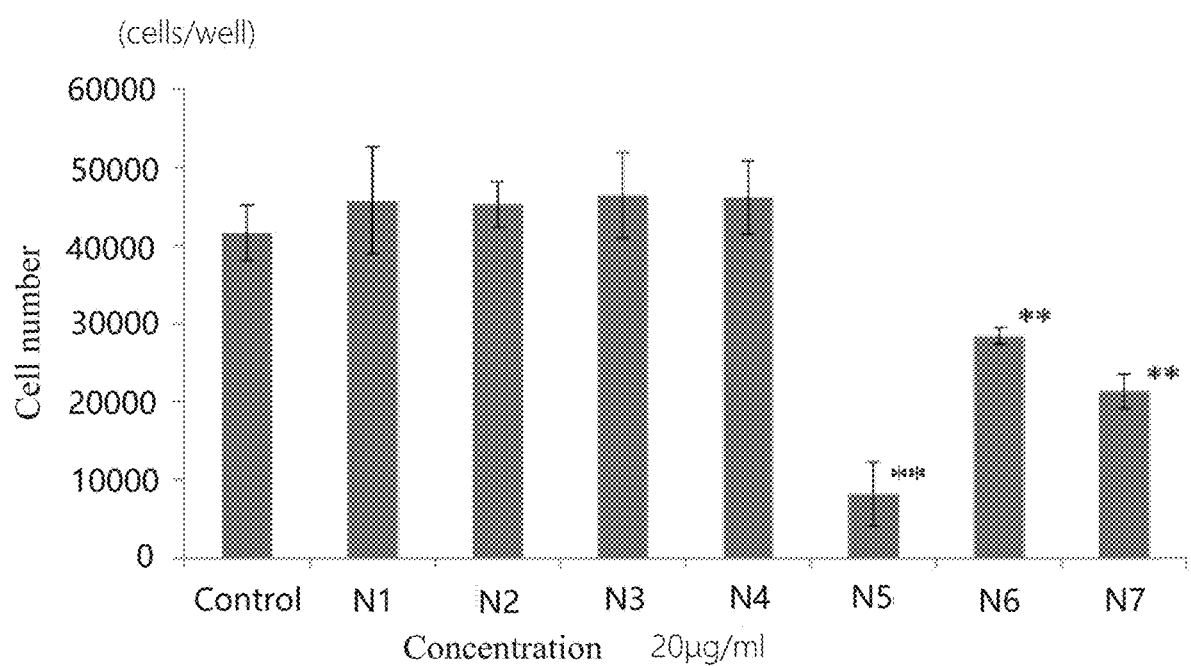
FIG. 4 is a graph showing the effects of Radix et Rhizoma Ginseng extracts on epidermal keratinocyte proliferation in a dermal papilla cell and keratinocyte double-layer culture system under the condition that the ginsenoside composition is at a concentration of 20 μg/ml.
Figure 5:
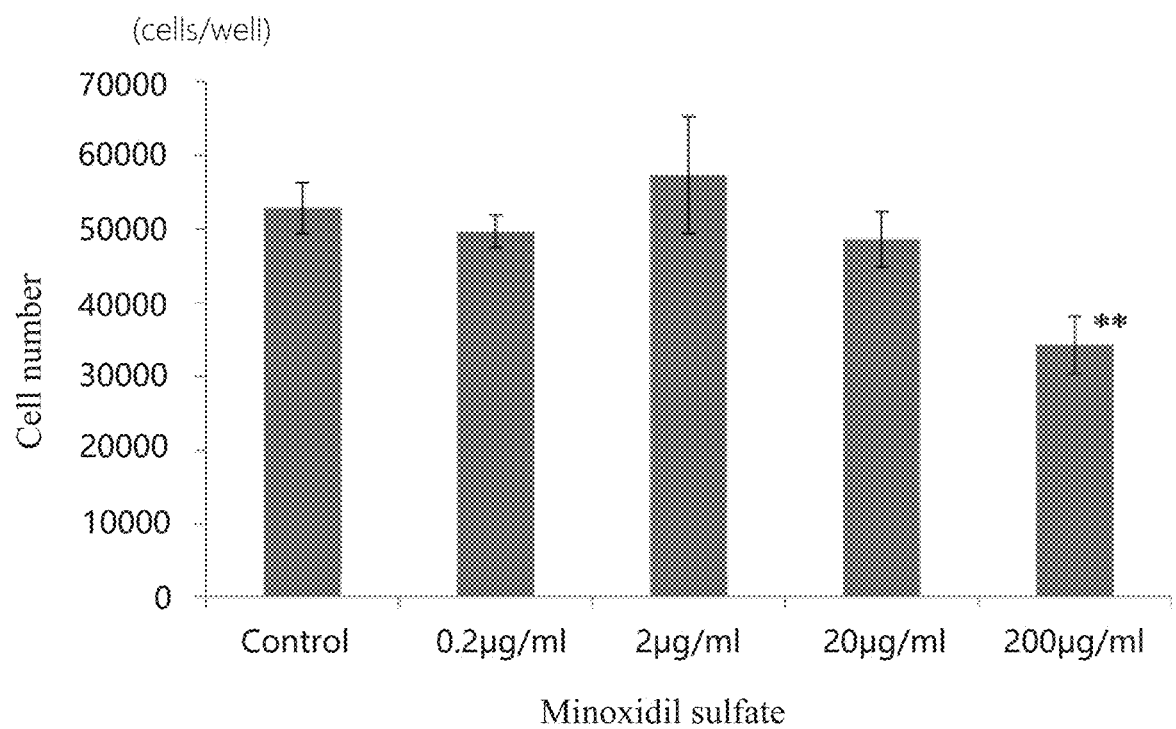
FIG. 5 is a graph showing the effects of Radix et Rhizoma Ginseng extracts on epidermal keratinocyte proliferation in a dermal papilla cell and keratinocyte double-layer culture system under minoxidil sulphate at different concentrations.

Referring to FIG. 3, FIG. 3 showed the effects of Radix et Rhizoma Ginseng extracts on epidermal keratinocyte proliferation in a dermal papilla cell and keratinocyte double-layer culture system under the condition that the ginsenoside composition was at a concentration of 2 µg/ml;

referring to FIG. 4, FIG. 4 showed the effects of Radix et Rhizoma Ginseng extracts on epidermal keratinocyte proliferation in a dermal papilla cell and keratinocyte double-layer culture system under the condition that the ginsenoside composition was at a concentration of 20 µg/ml;

referring to FIG. 5, FIG. 5 showed the effects of Radix et Rhizoma Ginseng extracts on epidermal keratinocyte proliferation in a dermal papilla cell and keratinocyte double-layer culture system under minoxidil sulphate at different concentrations;

it was found through experiments with the dermal papilla cell and keratinocyte double-layer culture system that the ginsenoside compositions N4 and 7 had an effect of promoting epidermal keratinocyte proliferation at a concentration of 2 µg/ml. Whereas the ginsenoside compositions N5, 6, 7 had an inhibitory effect or cytotoxic effect at a concentration of 20 µg/ml. The positive control Minoxidil sulfate (0.2 µg/ml, 2 µg/ml, 20 µg/ml, 200 µg/ml) was found to have no effect in promoting keratinocyte proliferation.

3. Effect of Radix Et Rhizoma Ginseng Extracts on 5α-Reductase Activity

5α-reductase was an enzyme that promoted the conversion of testosterone to 5α-dihydrotestosterone. An NAD cycling method was used in the experiment for assaying the effects of Radix et Rhizoma Ginseng extracts on 5α-reductase activity.

A Solution A was prepared by adding 520 µl of a buffer solution (pH 5.0) containing 0.3 M of sucrose/1 mM of dithiothreitol/40 mM of potassium phosphate, 80 µl of 100 µM testosterone, 40 µl of 16 µM NADPH in a 1.5 ml test tube. 83 µl of the solution A, 1 µl of the Radix et Rhizoma Ginseng extracts and 16 µl of Rat liver microsome were taken for culture for 20 minutes. After heating at a temperature of 80° C. for 5 minutes, 600 µl of a Tris-HCl buffer solution (pH 9.8) and 40 µl of 20 mM thio-NAD were added for continued culture for 10 minutes. After centrifugation, 100 µl was taken and added into the microwell plate, followed by the addition of 10 µl of 400 U/ml 3α-HSD, and the absorbance was determined at 400 nm within 30 minutes. Finasteride (40 nM) was a positive control.

Figure 6:
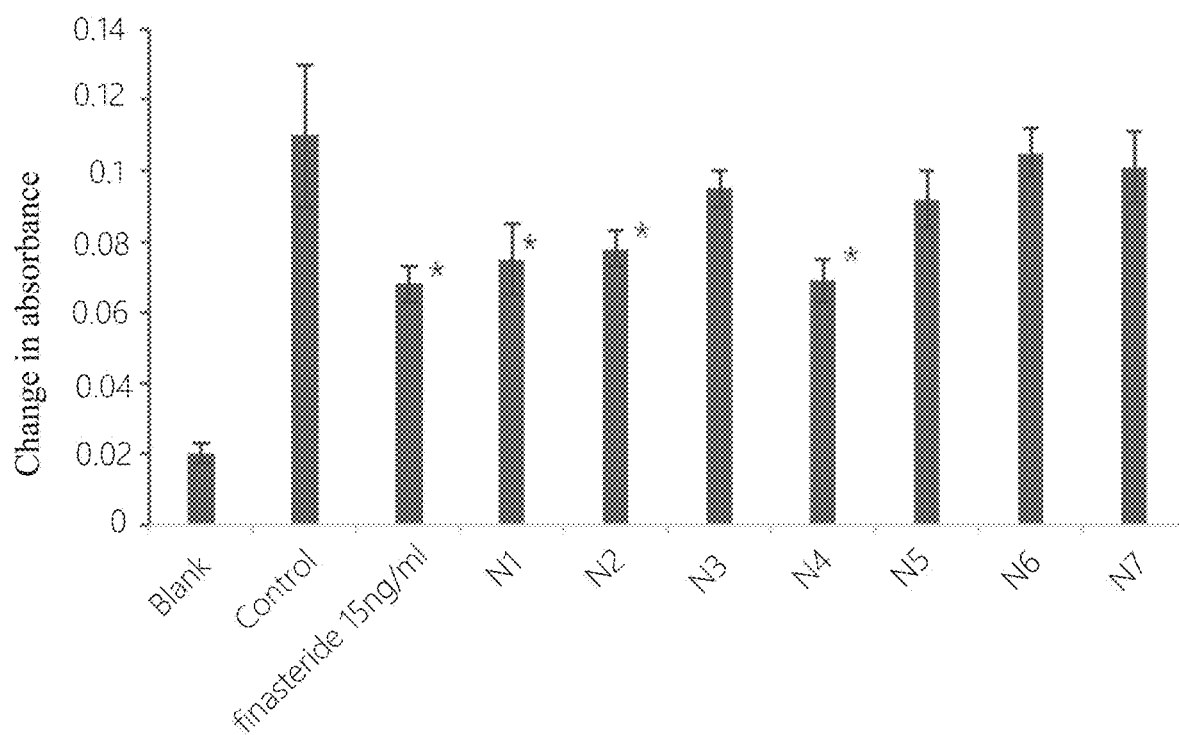
FIG. 6 is a graph showing the effects of ginsenoside compositions N1-N7 on 5α-reductase activity.

FIG. 6 is a graph showing the effects of ginsenoside compositions on 5α-reductase activity;

the ginsenoside compositions N1, 2, 4 (200 µg/ml) had an inhibitory effect on the 5 α-reductase activity. The intensity of the inhibitory effect was comparable to the effect of 15 ng/ml (40 nM) finasteride.

Figure 7:
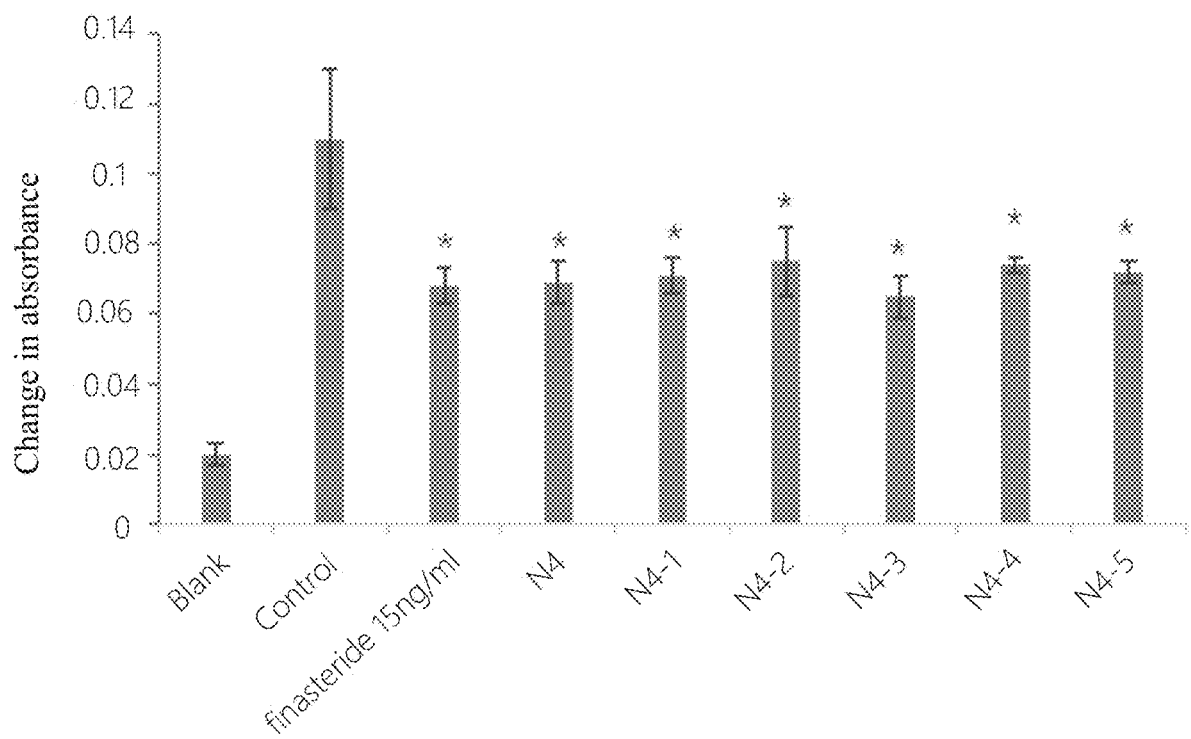
FIG. 7 is a graph showing the effects of ginsenoside compositions N4, N4-1, 2, 3, 4, 5 on 5α-reductase activity.

FIG. 7 showed that the ginsenoside compositions N4, N4-1, 2, 3, 4, 5 (200 µg/ml) had an inhibitory effect on 5 α-reductase activity. The strength of the inhibitory effect was almost comparable.

4. Effects of Radix Et Rhizoma Ginseng Extracts on Alkaline Phosphatase Activity A human dermal papilla cell solution at a concentration of 100,000 cells/ml was prepared and added to a 96 Well Cell Culture Plate at an amount of 100 µl/well (n=3). and cultured for 1 day. The concentration of the samples to be tested ranged from 0.2 µg/ml to 200 µg/ml, and the concentration of minoxidil sulphate ranged from 0.02 µg/ml to 20 µg/ml. After culture for 3 days, after fixation with 4% PFA, PBS was used for washing, and the alkaline phosphatase activity was determined using a BCIP-NBT solution at 405 nm.

Figure 8:
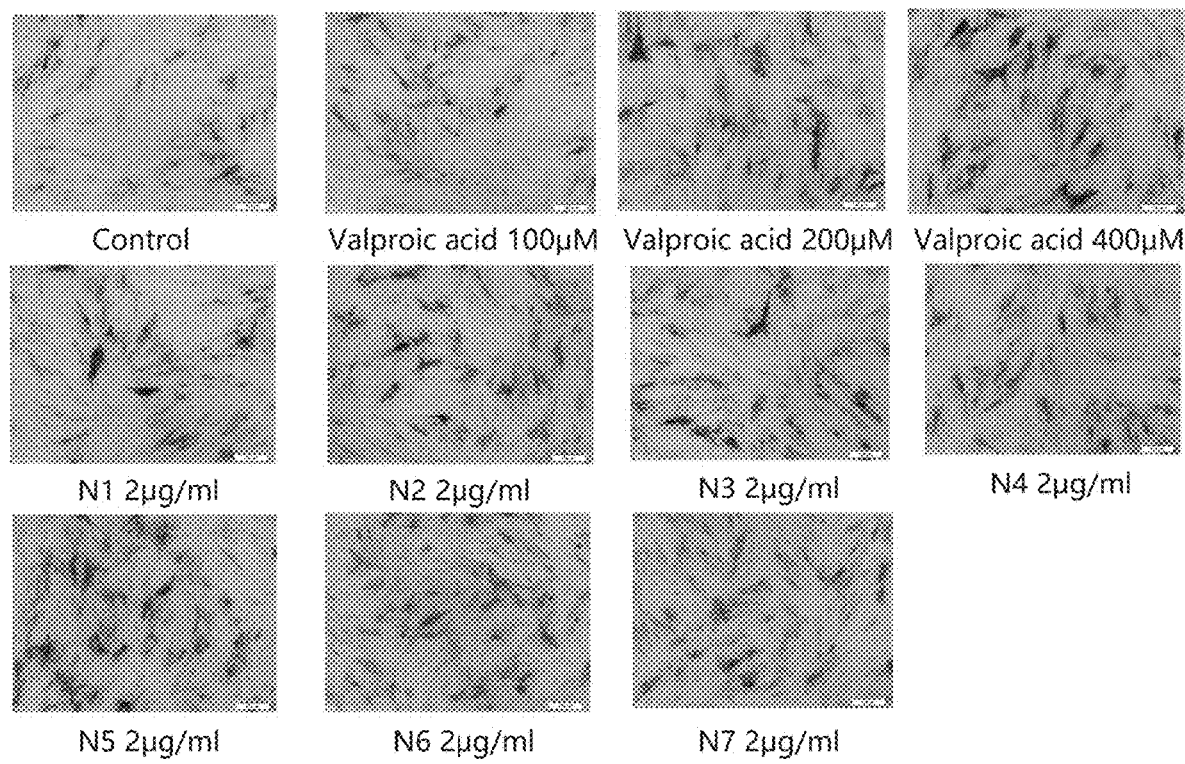
FIG. 8 is graph showing staining of the effects of the ginsenoside compositions at a concentration of 2 μg/ml on the activity of alkaline phosphatase of cultured dermal papilla cells.
Figure 9:
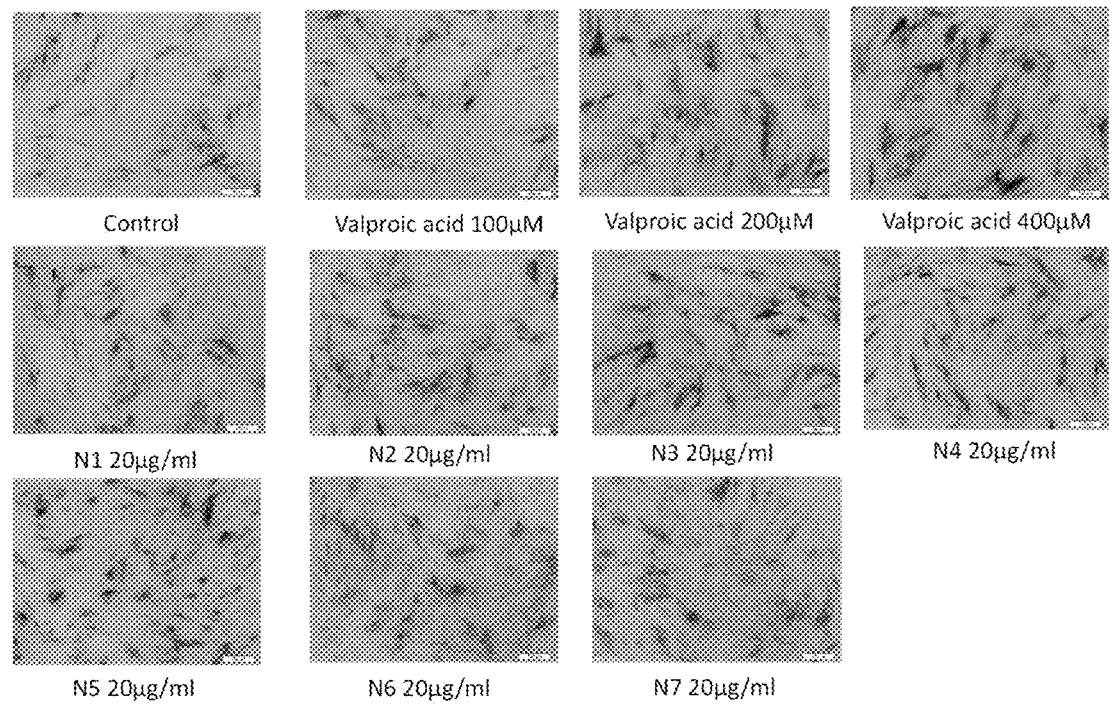
FIG. 9 is graph showing staining of the effects of the ginsenoside compositions at a concentration of 20 μg/ml on the activity of alkaline phosphatase of cultured dermal papilla cells.
Figure 10:
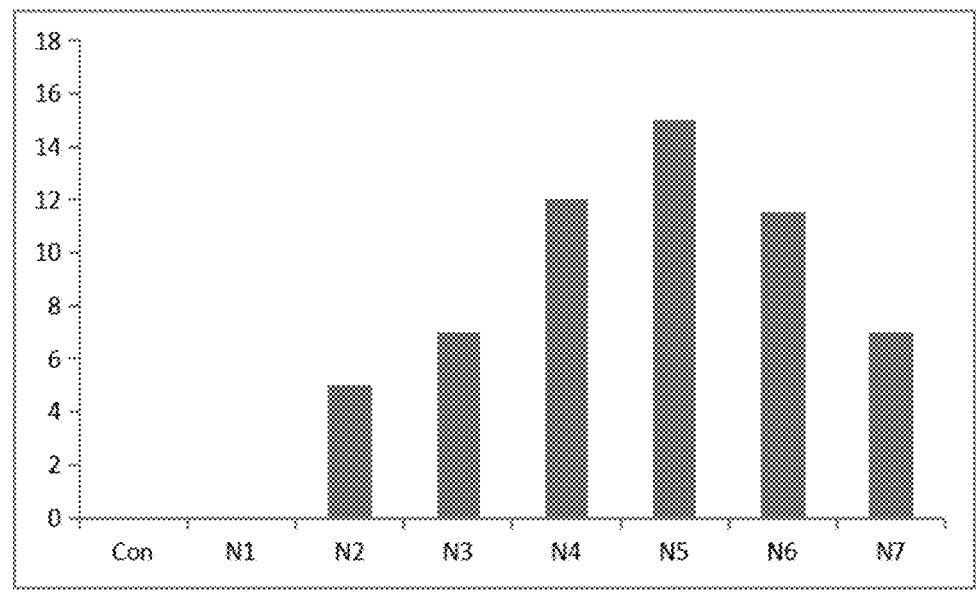
FIG. 10 is a graph showing the effects of the ginsenoside compositions on activity of alkaline phosphatase of cultured dermal papilla cells.
Figure 11:
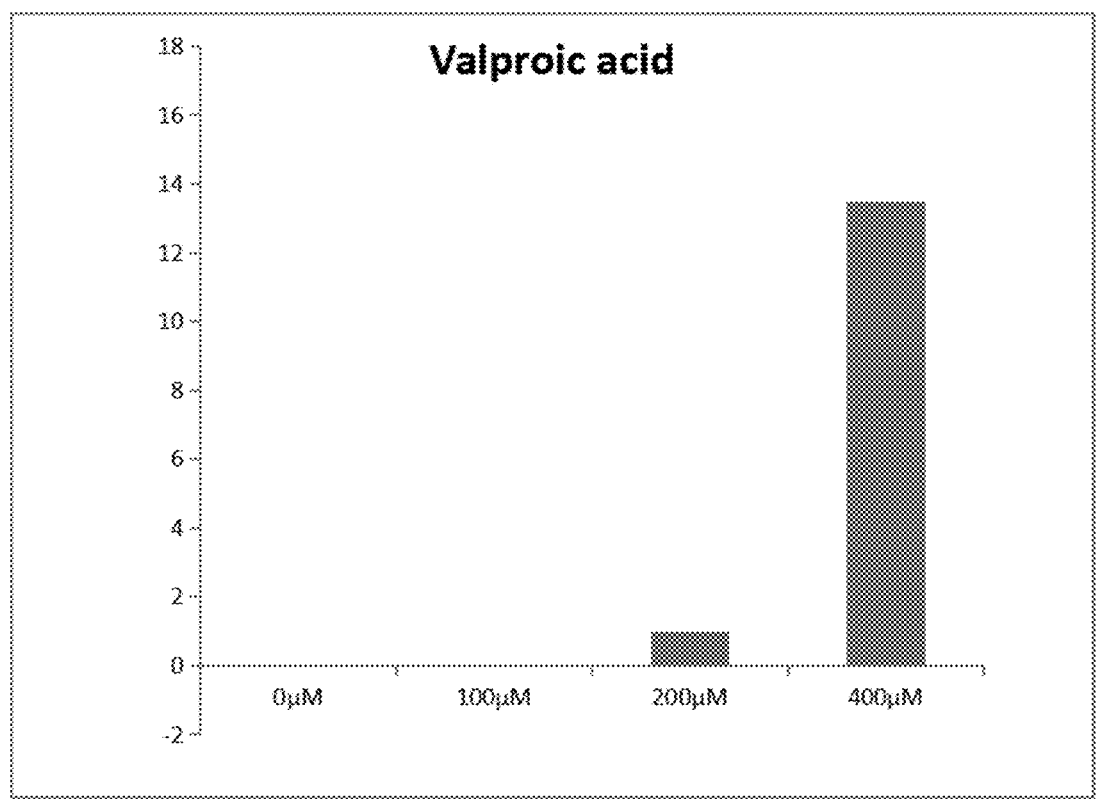
FIG. 11 is a graph showing the effects of valproic acid as a positive control at different concentrations on activity of alkaline phosphatase of cultured dermal papilla cells.

FIG. 8 is a graph showing staining of the effects of the ginsenoside compositions at a concentration of 2 µg/ml on the activity of alkaline phosphatase of cultured dermal papilla cells; and valproic acid was used as a positive control;

FIG. 9 is a graph showing staining of the effects of the ginsenoside compositions at a concentration of 20 µg/ml on the activity of alkaline phosphatase of cultured dermal papilla cells; and valproic acid was used as a positive control;

FIG. 10 is a graph showing the effects of the ginsenoside compositions on the activity of alkaline phosphatase of cultured dermal papilla cells;

FIG. 11 is a graph showing the effects of valproic acid as a positive control at different concentrations on activity of alkaline phosphatase of cultured dermal papilla cells.

Result Analysis:

1. the ginsenoside composition N5, the ginsenoside composition N6 and the ginsenoside composition N7 have stronger cytotoxicity than other Radix et Rhizoma Ginseng extracts (referring to FIG. 4).
2. Referring to FIGS. 1-4, the ginsenoside composition N4 has the effect of promoting the epidermal keratinocyte proliferation effect, and it is also found that it promotes the epidermal keratinocyte proliferation effect when tested with the dermal papilla cell and keratinocyte double-layer culture system.
3. Referring to FIG. 6, the ginsenoside composition N1 and the ginsenoside compositions N2, N4 have the effect of inhibiting 5α-reductase activity, suggesting that N1 and N2, N4 can significantly prevent male hair loss.
4. Referring to FIG. 7, the ginsenoside compositions N4, N4-1, 2, 3, 4, 5 have approximately consistent effects of inhibiting 5α-reductase activity, suggesting that N4, N4-1, 2, 3, 4, 5 can all effectively and significantly prevent male hair loss.

5. Referring to FIGS. 8-10, the ginsenoside composition N4, the ginsenoside composition N5 and the ginsenoside composition N6 have the effect of promoting alkaline phosphatase activity of cultured dermal papilla cells, suggesting that N4, N5, N6 have hair developing and hair proliferating efficacy.

In conclusion, N1, N2, N4 have efficacy in preventing male hair loss; N4, N5, N6 have hair developing and hair proliferating efficacy; and N5, N6, N7 have cytotoxicity;

N4 is one of the most commercially promising components overall from the point of view of promoting epidermal keratinocyte proliferation, hair loss prevention, hair development, hair proliferation, etc.

As a more effective means, it is recommended to combine any one of N1, N2, N4 with any one of N4, N5, N6;

and more effectively, it is recommended to combine either of N1, N2 with N4.

The formula of N4 according to the present invention was delivered to Shanxi Biocell General Testing Co. Ltd. under a trade name of "Canshi® Night SPC" for "In Vitro Hair Loss Efficacy Test"; and "ChronoShen® Night SPC" was a butanediol solution containing 1% of N4 ginsenoside. Therein, N4 was the only ingredient with active efficacy, and the others were co-solvents and preservative ingredients having no hair loss prevention or hair development functions. This test was divided into four parts; the first part was to perform a cytotoxicity assay based on the dermal papilla cells to determine the safe dosing concentration of the sample on the dermal papilla cells; the second part was to stimulate the dermal papilla cells with dihydrotestosterone (DHT) to evaluate the hair loss prevention and hair growth efficacy of the test sample by detecting the VEGF content and DKK1 gene change conditions after the sample acts on the dermal papilla cells; the third part was to evaluate the hair growth efficacy of the test sample based on the dermal papilla cells by detecting the cell proliferation after the sample acts on the cell; and the fourth part was to evaluate the hair loss prevention efficacy of the sample to be tested based on the in vitro inhibition of 5α-reductase activity.

Test Report Number: G522-2210027; Test Date: Aug. 25-Sep. 25, 2022; Test Conclusions of the test Report Number G522-2210027 include that, compared with the BC group, the cell proliferation rate of the PC group was significantly increased, indicating that the positive control of this test was effective, compared with the BC group, the cell viability at 24 h after administration of samples "Canshi® Night SPC"/"ChronoShen® Night SPC"-0.5% showed a significant increase trend, and the cell proliferation rate was 14.30%, based on the dermal papilla cells, compared with the control group, the VEGF content of samples "ChronoShen® Night SPC"/"ChronoShen® Night SPC" at a concentration of 0.5% (v/v) was significantly increased with an increase rate of 17.40%, the DKK1 gene expression was significantly downregulated with a downregulating rate of 26.06%, and the cell proliferation was significantly increased with an increase rate of 14.30% at 24 h after administration, indicating that at this concentration, the samples achieved the hair loss prevention effect by increasing the VEGF content and promoting DKK1 gene expression and cell proliferation.

Test Report Number: G522-2209047; Test Date: Aug. 24-Sep. 4, 2022; Test Conclusions of the test Report Number G522-2209047 include that, androgenetic alopecia (AGA) was one of the most common types of alopecia, androgenic alopecia was related to androgen levels, and after androgen secretion in the body, androgen bound to 5α-reductase in the body and was reduced to dihydrotestosterone (DHT), resulting in androgenic alopecia, compared with the control group, at concentrations of 5.00%, 0.50%, 0.05%, samples Canshi® Night SPC/ChronoShen® Night SPC had a significantly increased 5α-reductase inhibition rate with the inhibition rates of 33.14%, 20.71%, 12.72%, respectively, indicating that the samples Canshi® Night SPC/ChronoShen® Night SPC could achieve the hair loss preventing efficacy by inhibiting 5α-reductase activity and alleviating androgen-induced hair loss.

The ingredients of the raw material "Canshi® Night SPC" for the aforementioned two test reports were as shown in Table 6 below:

TABLE 6

Formula table

| Component | Component content (%) |
|---|---|
| N4 | 1 |
| 1,3-butanediol | 98 |
| 1,2-hexanediol | 1 |

The aforementioned test results also demonstrate that the formula of N4 has better hair loss prevention and hair development effects.

At the same time, the aforementioned "Canshi® Night SPC" was added to a common essence (see formula table 7) to form a hair-loss-preventing essence, wherein "Canshi® Night SPC" was the only ingredient with active efficacy, and others were co-solvents and preservative ingredients having no hair loss prevention or hair development functions; and the hair-loss-preventing essence was sent to Centre Testing International Group Co., Ltd. for human experiments with the sample number HBO00942001, and the experiments were classified into hair loss counting tests, overall hair density tests and topical skin hair tests;

TABLE 7

Formula table of "Canshi ® Night SPC" scalp essence

| Phase | Name of component | Percentage content (%) | Effect |
|---|---|---|---|
| A | Butanediol | 4.00 | Humectant |
|  | Carbomer 981 | 0.15 | Thickener |
|  | Small molecule sodium hyaluronate | 0.05 | Scalp moisturizing |
|  | Water | To 100 | Solvent |
| B | Sodium hydroxide | 0.012 | pH regulator |
| C | Ethyl alcohol | 8.00 | Solvent |
|  | Piperitol | 0.04 | Cooling and relieving itching |
|  | Borneol | 0.06 | Cooling and relieving itching |
| D | ChronoShen ® Night SPC (water, butanediol, ginsenoside N4, 1,2-hexanediol) | 2.00 | Scalp anti-aging, soothing, oil control, hair loss prevention |
|  | Glycerol caprylate, octyl hydroxamic acid | 0.80 | Preservative |
|  | 1,2-hexanediol | 1.00 | Anti-corrosion and efficiency enhancement |

Process:
water was added into a water pan, slowly sprinkled with carbomer, stirring was started, and temperature rose to 85° C.;
the water pan was pumped into the main pan, added with a premix of butanediol and sodium hyaluronate, kept at 85° C., and stirred uniformly;

it was cooled to 60° C., added with an aqueous solution of a phase B, and stirred uniformly;

it was cooled to 40° C., added with a premix of phase C, stirred uniformly, added with a phase D in sequence, and stirred uniformly;

and materials were taken for testing, and discharging was conducted after qualification with pH 5.5-6.5.

Physicochemical Indicators:

Appearance: transparent essence-like liquid
pH: 5.5-6.5

See Table 8 for the hair loss count test results;

TABLE 8

| Descriptive | Hair loss count test results | | | |
|---|---|---|---|---|
| statistics | D 0 | D 28 | D 56 | D 84 |
| Number of people | 10 | 10 | 10 | 10 |
| Mean value | 21 | 19 | 13 | 7 |
| Standard deviation | 7 | 11 | 11 | 5 |
| Maximum value | 32 | 42 | 40 | 18 |
| Minimum value | 11 | 4 | 5 | 0 |
| Mid-value | 20 | 17 | 9 | 7 |

It could be found through the aforementioned test that 10 subjects had a reduction in hair loss count of 9.52% after 28 days of use of the sample; had a reduction in hair loss count of 38.10% after 56 days of use of the sample; and had a reduction in hair loss count of 66.67% after 84 days of use of the sample. During the product usage period, the hair loss conditions of the subjects were improved significantly with the extension of usage time.

See Table 9 for hair density tests;

TABLE 9

| Descriptive | Hair density statistics | | | |
|---|---|---|---|---|
| statistics | D 0 | D 28 | D 56 | D 84 |
| Number of people | 10 | 10 | 10 | 10 |
| Mean value | 3.8 | 4.0 | 4.3 | 4.5 |
| Standard deviation | 0.8 | 0.9 | 0.8 | 0.8 |
| Maximum value | 4.8 | 5.0 | 5.0 | 5.0 |
| Minimum value | 2.0 | 2.0 | 2.3 | 2.5 |
| Mid-value | 4.0 | 4.2 | 4.5 | 4.5 |

As could be seen from the aforementioned tests, with the increase of usage time, 10 subjects had an increase in overall hair density of 5.26% after 28 days of use of the sample; had an increase in overall hair density of 13.16% after 56 days of use of the sample; and had an increase in overall hair density of 18.42% after 84 days of use of the sample.

Figure 12:
FIG. 12 is a photomicrograph of the scalp of parts of subjects in a first part of human tests.
Figure 13:
FIG. 13 is a photograph of hair of parts of subjects in the first part of human tests.

FIG. 12 is a photomicrograph of the scalp of parts of subjects;

FIG. 13 is a photograph of hair of parts of subjects.

As could be seen from human tests, the composition N4 according to the present invention could significantly inhibit hair loss and increase hair density when used as an essence.

It could be seen by the aforementioned tests that:
when different ginsenosides were adopted for combined compounding, the triol-type rare ginsenoside secondary glycoside combination (N4 and N5), the diol-type rare ginsenoside secondary glycoside combination (N6, N7), the mixed native ginsenoside (N1), the diol-type ginsenoside (N2) and the triol-type ginsenoside (N3) showed different trends, wherein N4 performed the best effect in multiple tests, being a combination worthy of subsequent ongoing studies;

Prominent contributions of the present invention are:
1. Different ginsenosides exhibit different characteristics, and they should be flexibly selected to be formulated based on the above experimental results according to product formula characteristics in the using process.
2. The present invention provides several groups of combinations with raw materials optimized as many as possible and the minimal usage amount so as to adapt to daily-use chemical formulas with different functions.

Part II Study on Compounding of Ginsenoside Compositions with Palmitoyl Tetrapeptide-7, Blue Copper Peptide and Ectoin Example 8

TABLE 10

| Formula table of ginsenoside-containing composition | |
|---|---|
| Component | Component content |
| Water | To 100 |
| Palmitoyl tetrapeptide-7 | 0.02 |
| Blue copper peptide | 0.02 |
| Ginsenoside | 0.2 |
| Ectoin | 1 |
| Butanediol | 20 |
| Preservative | 1.5 |

N1, N2, N3, N4, N5, N6, N7 were added to the ginsenoside compositions at a concentration of 0.2% respectively to obtain 7 ginsenoside-containing compositions, and the ginsenoside-containing compositions were added to the formula shown in Table 11 to obtain samples 1-7;

See Table 11 for the formula of the hair-loss-preventing essence:

TABLE 11

| Phase | Name of component | Percentage content (%) | Effect |
|---|---|---|---|
| A | Butanediol | 4.00 | Humectant |
| | Carbomer 981 | 0.15 | Thickener |
| | Small molecule sodium hyaluronate | 0.05 | Scalp moisturizing |
| | Water | To 100 | Solvent |
| B | Sodium hydroxide | 0.012 | pH regulator |
| C | Ethyl alcohol | 8.00 | Solvent |
| | Piperitol | 0.04 | Cooling and relieving itching |
| | Borneol | 0.06 | Cooling and relieving itching |
| D | Ginsenoside compositions (water, butanediol, ginsenoside, palmitoyl tetrapeptide-7, tripeptide-1 copper, ectoin, 1,2-hexandiol) | 10.00 | Scalp anti-aging, soothing, oil control, hair loss prevention |
| | Glycerol caprylate, octyl hydroxamic acid | 0.80 | Preservative |
| | 1,2-hexanediol | 1.00 | Anti-corrosion and efficiency enhancement |

The ginsenoside in sample 1 was N1; the ginsenoside in sample 2 was N2; the ginsenoside in sample 3 was N3; the ginsenoside in sample 4 was N4; the ginsenoside in sample 5 was N5; the ginsenoside in sample 6 was N6; and the ginsenoside in sample 7 was N7; and by performing the preliminary hair loss prevention test inside the laboratory, it was found that sample 4 performed the best in terms of hair loss prevention, hair growth, scalp maintenance and hair development.

Sample 4 was sent to Centre Testing International Group Co., Ltd. under the name of "ChronoShen® Kpdens N Hair-loss-preventing Essence"; and the delivery time was Sep. 23, 2022, and the detection time was Oct. 14, 2022-Jan. 6, 2023;

The testing items were the same as those in the human test in the first part, the experiments were divided into hair loss tests, overall hair density tests and local skin hair density tests;

See Table 12 for the hair loss test results;

TABLE 12

| Descriptive | Hair loss test results | | | |
|---|---|---|---|---|
| | Head | | | |
| statistics | D 0 | D 28 | D 56 | D 84 |
| Number of people | 10 | 10 | 10 | 10 |
| Mean value | 30 | 13 | 20 | 12 |
| Standard deviation | 20 | 8 | 14 | 5 |
| Maximum value | 79 | 31 | 50 | 22 |
| Minimum value | 13 | 5 | 5 | 6 |
| Mid-value | 24 | 12 | 16 | 12 |

It was found through the aforementioned tests that 10 subjects had a reduction in hair loss count of 56.67% after 28 days of use of the sample; and had a reduction in hair loss count of 60% after 84 days of use of the sample. During the product usage period, the hair loss conditions of the subjects were improved significantly with the extension of usage time.

See Table 13 for the overall hair density test;

TABLE 13

| Descriptive | Hair density statistics | | | |
|---|---|---|---|---|
| | Head | | | |
| statistics | D 0 | D 28 | D 56 | D 84 |
| Number of people | 10 | 10 | 10 | 10 |
| Mean value | 3.3 | 4.0 | 4.6 | 4.4 |
| Standard deviation | 0.9 | 0.9 | 0.4 | 0.6 |
| Maximum value | 4.3 | 5.3 | 5.5 | 5.3 |
| Minimum value | 1.0 | 2.0 | 4.3 | 3.3 |
| Mid-value | 3.5 | 4.0 | 4.4 | 4.4 |

It was found through the aforementioned tests that 10 subjects had an increase in overall hair density of 21.21% after 28 days of use of the sample; had an increase in overall hair density of 39.39% after 56 days of use of the sample; and had an increase in overall hair density of 33.33% after 84 days of use of the sample.

Figures 14, 15:
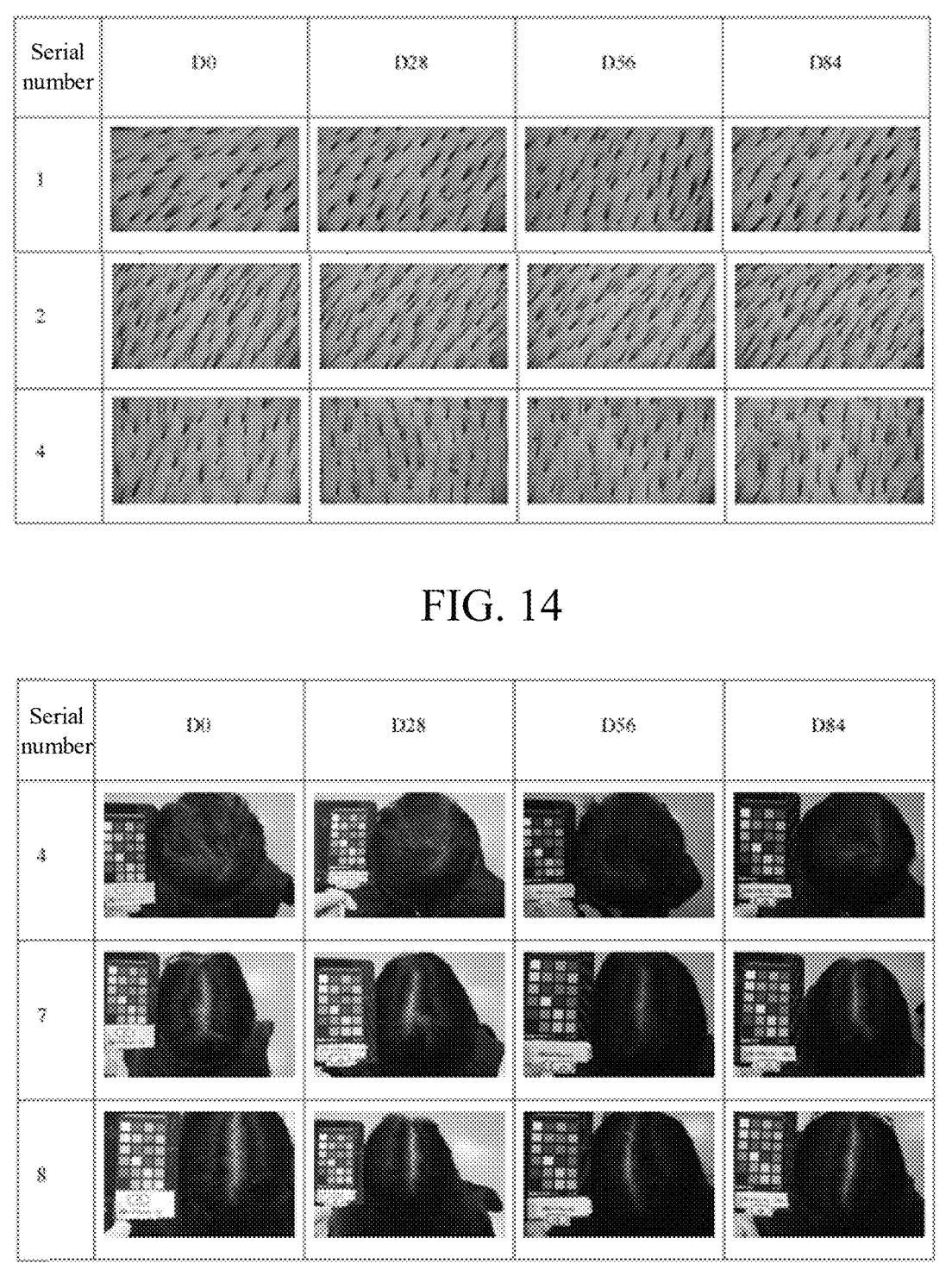

FIG. 14 is a photomicrograph of the scalp of parts of subjects;

FIG. 15 is a photograph of hair of parts of subjects.

It was found through the human tests that the "ChronoShen® Kpdens N Hair-loss-preventing Essence" of the present invention was able to significantly inhibit hair loss and increase hair density.

From a lateral comparison with the first part of the human experiments, it could be seen that:

for the essence of the first part of the human experiments and the essence of the second part of the human experiments, under the condition that the usage amount of ginsenoside compositions was the same, the "ChronoShen® Kpdens N Hair-loss-preventing Essence" of the present invention had the following advantages:

1. It could be found by comparing Table 8 and Table 12 that the "ChronoShen® Kpdens N Hair-loss-preventing Essence" was able to achieve the hair loss preventing effect quickly, and was faster in effect taking than "Canshi® Night SPC".
2. It could be found by comparing Table 9 and Table 13 that the "ChronoShen® Kpdens N Hair-loss-preventing Essence" had a larger magnitude of increase in hair density;
3. It could be found through FIGS. 12-13 and FIGS. 14-15 that the "ChronoShen® Kpdens N Hair-loss-preventing Essence" had better hair density and hair quality.

Thus, we believed that the ginsenoside compositions of the present invention, in particular the combination of N4 with palmitoyl tetrapeptide-7, blue copper peptide and ectoin achieved optimal fast acting and consistently-increased hair loss prevention, hair growth, scalp care and hair development effects.

What is claimed is:

1. A ginsenoside-containing composition, comprising the following components in parts by weight:
    0.001-0.05 parts of palmitoyl tetrapeptide-7,
    0.001-0.05 parts of blue copper peptide,
    0.1-10 parts of ectoin, and
    0.05-5 parts of a ginsenoside composition;
    wherein the ginsenoside composition is any one or more groups of ginsenoside compositions selected from groups consisting of N1, N2, and N4;
    wherein the N1 comprises the following components:
    12-28 wt % of ginsenoside Rg1,
    10-16 wt % of ginsenoside Re,
    12-28 wt % of ginsenoside Rb1,
    13-22 wt % of ginsenoside Rc,
    13-22 wt % of ginsenoside Rb2, and
    7-13 wt % of ginsenoside Rd;
    wherein the N2 comprises the following components:
    30-50 wt % of ginsenoside Rg1, and
    48-72 wt % of ginsenoside Re;
    wherein the N4 comprises the following components:
    8-16 wt % of 20(S)-ginsenoside Rg2,
    7-15 wt % of 20(R)-ginsenoside Rg2,
    17-25 wt % of 20(S)-ginsenoside Rh1,
    16-23 wt % of 20(R)-ginsenoside Rh1,
    5-12 wt % of ginsenoside Rk3, and
    16-26 wt % of ginsenoside Rh4;
    and a sum of the components of each of N1, N2, N4 is 100%.

2. The ginsenoside-containing composition according to claim 1, wherein the N1 comprises the following components:
    18-22 wt % of ginsenoside Rg1,
    12-15 wt % of ginsenoside Re,
    18-22 wt % of ginsenoside Rb1,
    15-19 wt % of ginsenoside Rc,
    16-20 wt % of ginsenoside Rb2, and
    9-11 wt % of ginsenoside Rd;
    wherein the N2 comprises the following components:
    35-45 wt % of ginsenoside Rg1, and
    55-65 wt % of ginsenoside Re;
    wherein the N4 comprises the following components:
    10-13 wt % of 20(S)-ginsenoside Rg2, 8-13 wt % of 20(R)-ginsenoside Rg2,
18-23 wt % of 20(S)-ginsenoside Rh1,
17-21 wt % of 20(R)-ginsenoside Rh1,
6-10 wt % of ginsenoside Rk3, and
18-22 wt % of ginsenoside Rh4;
and a sum of the components of N1, N2, N4 is 100%.

3. The ginsenoside-containing composition according to claim 1, wherein the ginsenoside compositions contain N4 and at least one of N1, N2.

4. The ginsenoside-containing composition according to claim 1, comprising the following components in parts by weight:
0.01-0.03 parts of palmitoyl tetrapeptide-7,
0.01-0.03 parts of blue copper peptide,
0.5-2 parts of ectoin, and
0.05-1 parts of the ginsenoside composition.

5. The ginsenoside-containing composition according to claim 1, comprising the following components in parts by weight:
0.02 parts of palmitoyl tetrapeptide-7,
0.02 parts of blue copper peptide,
1 part of ectoin, and
0.25 parts of the ginsenoside composition.

6. A daily-use chemical acting on hair, comprising the composition according to claim 1; wherein the composition accounts for 0.01-50 wt % of a total weight of the daily-use chemical.

7. The daily-use chemical acting on hair according to claim 6, wherein the composition accounts for 0.01-20 wt % of the total weight of the daily-use chemical.

8. The daily-use chemical acting on hair according to claim 6, wherein the daily-use chemical is shampoo, a hair conditioner, lyophilized powder, an essence, shampoo spray, hair cream, hair lotion.

* * * * *